United States Patent
Darcey

[19]

[11] Patent Number: 5,957,871
[45] Date of Patent: Sep. 28, 1999

[54] CUSTOM-FITTED ANKLE SPLINT PRODUCT

[75] Inventor: Thomas D. Darcey, Mooresville, N.C.

[73] Assignee: Smith & Nephew, Inc., Charlotte, N.C.

[21] Appl. No.: 09/209,186

[22] Filed: Dec. 10, 1998

Related U.S. Application Data

[63] Continuation-in-part of application No. 09/143,755, Aug. 31, 1998, which is a continuation-in-part of application No. 09/049,723, Mar. 27, 1998.

[51] Int. Cl.$^6$ ........................................................ A61F 5/00
[52] U.S. Cl. .................................... 602/12; 602/5; 602/6; 602/8; 602/27
[58] Field of Search ................................ 602/12, 5, 6, 8, 602/27, 78

[56] References Cited

U.S. PATENT DOCUMENTS

| | | |
|---|---|---|
| 4,287,920 | 9/1981 | Johnson, Jr. . |
| 4,442,833 | 4/1984 | Dahlen et al. . |
| 4,502,479 | 3/1985 | Garwood et al. . |
| 4,570,622 | 2/1986 | von Bonin et al. . |
| 4,899,738 | 2/1990 | Parker . |
| 5,088,478 | 2/1992 | Grim . |
| 5,199,941 | 4/1993 | Makinen . |
| 5,217,431 | 6/1993 | Toronto et al. . |
| 5,637,077 | 6/1997 | Parker . |

*Primary Examiner*—John G. Weiss
*Assistant Examiner*—Kelvin Hart
*Attorney, Agent, or Firm*—Adams Law Firm, P.A.

[57] ABSTRACT

An ankle splint product includes an ankle splint for being custom-formed to the shape of an ankle while flexible and upon hardening providing a rigid, supporting custom fit. The ankle splint product includes an outer container formed of moisture-impervious material, and first and second flexible ankle splint segments positioned in the container in substantially moisture-free conditions and sealed therein against entry of moisture until use. Each of the first and second ankle splint segments includes an elongate substrate and a reactive system impregnated into or coated onto the substrate. The system remains stable when maintained in substantially moisture-free conditions and hardens upon exposure to moisture to form a rigid, self supporting structure. An elongate, flexible protective pad is positioned on one side of the substrate along its length to provide a cushioning barrier between the substrate and the skin of a patient when the ankle splint is in use. An elongate outer cover covers the substrate on the side opposite the protective pad. A flexible cushion insert has a first major surface overlying the protective pad and an opposing second major surface adapted for residing adjacent an ankle bone of the patient. The cushion insert cooperates with the protective pad to further protect and cushion the ankle of the patient when the ankle splint is in use. At least one elasticized strap is provided to hold the splint segments in place on the lower leg and ankle. The strap provides enhanced conformance to the leg, and reduces edema and increases blood flow by providing controlled pressure to the leg as the patient walks or otherwise exercises the injured limb.

7 Claims, 14 Drawing Sheets

CUSTOM-FITTED ANKLE SPLINT PRODUCT

TECHNICAL FIELD AND BACKGROUND OF THE INVENTION

This application is a continuation-in-part of Ser. No. 09/143,755, filed on Aug. 31, 1998, which is a continuation-in-part of Ser. No. 09/049,723, filed on Mar. 27, 1998.

This invention relates to a custom-fitted ankle splint product.

The invention has particular application in the orthopedic medical field, where ankle sprains or fractures are often supported and immobilized with a splint or brace so that the patient can continue to walk while the injury heals. One typical such injury is a sprain of the anterior talofibular ligament at the interior margin of the lateral malleolus. In such cases, it is essential to splint the ankle in such a way as to stabilize the ankle against eversion and inversion while permitting dorsiflexion and planoflexion necessary for normal walking and therapeutic exercise. It is also desirable for the splint to be sufficiently compact to fit within a conventional shoe. This facilitates sufficient use of the injured ankle during healing so that muscle atrophy is avoided or minimized.

The invention takes advantage of polymer chemistry to permit quick and easy molding of a splint to the ankle. Shock attenuation is increased since the custom fit provides spreads contact between the splint and the ankle over a wider surface area. Similarly, the close, custom fit is in distinct contrast to so-called "one size fits all" braces or splints wherein a rigid outer shell provides support, and a relatively thick cushioning pad, for example, an inflatable bladder, must be utilized to fill the voids created between the "one sized" rigid shell and the foot, ankle and lower leg.

Therefore, in the particular embodiment of the invention disclosed in this application, the splint will accommodate a wide range of sizes and can be fitted to either the right or left ankle. Thus, a much reduced inventory of splints is required. This feature also substantially reduces design and manufacturing costs, and promotes use through ease of fitting. The custom-fit of the splint permits easy removal for bathing, dressing or adjustment, and easy and mistake-proof replacement even by children.

Prior art ankle splints include numerous types of splints and braces which typically include a soft component to place near the skin and a hard, shell-like preformed outer cover having a shape approximating a "normal" ankle. The soft component, for example, fiber padding, foam or an air bladder, is intended not only to provide a cushion, but also to accommodate itself to the varying configurations of differing sized and shaped body parts. For this reason, the cushioned part is substantially greater in thickness than required merely to provide the required amount of shock attenuation and protection from the rigid substrate. Such devices are sufficiently "generic" in size and shape that they usually are required to be held in place by straps or bands.

Other prior art ankle braces include pads which are constructed of thermosetting materials which are heated and then formed to the body while heated. These products require a source of heat, and are susceptible to either over-or-underheating. In addition, body heat itself can soften or increase the flexibility of the pad, thereby decreasing the effectiveness of the protection offered by the pad.

Applicant's prior U.S. Pat. No. 5,637,077 provides a solution to some of the problems described above, but is a unitary structure which has definite forward and reward sides. Also, because the opposing sides of the splint are integrally-formed to each other by means of a unitary heel support member, lengthwise adjustment of the splint by shortening or lengthening the heel support is not possible.

The present invention permits quick and easy application of an ankle splint to a body part in such a way as to achieve a true custom fit. The moisture curable resin system used results in a very rigid ankle splint which holds the shape of the molded splint to a very high degree. No heat is required, and a source of water is the only additional material necessary to achieve a cure. Atmospheric moisture alone will cure the splint into its hardened position in a relatively short period of time, but in practice the resin in or on the splint will typically be activated by dipping in water and then removing the excess by rolling the splint in a towel immediately before application.

The splint according to this invention includes at least one elastic strap which holds the splint on the lower leg and foot, and provides stimulation to the injured limb as the patient is rehabilitated through exercise, including walking. The strap is intended to be used during the later stages of recovery, and offers distinct advantages over the use of prior art elastic wraps.

SUMMARY OF THE INVENTION

Therefore, it is an object of the invention to provide a custom-moldable ankle splint product which includes at least one elastic strap for holding the rigid splint segments against the leg and ankle.

It is another object of the invention to provide a custom-moldable splint product which includes at least one elastic strap for conformably holding the rigid splint segments against the generally conical shape of the leg and ankle.

It is another object of the invention to provide a custom-moldable splint product which includes at least one elastic strap for conformably holding the rigid splint segments against the generally conical shape of the leg and ankle while providing controlled pressure to the injured limb during rehabilitation.

It is another object of the invention to provide a custom-moldable splint product which includes at least one elastic strap for conformably holding the rigid splint segments against the generally conical shape of the leg and ankle while providing controlled pressure to the injured limb during rehabilitation.

It is another object of the invention to provide a custom-moldable splint product which includes at least one elastic strap for conformably holding the rigid splint segments against the generally conical shape of the leg and ankle while providing a controlled pumping action to the injured limb during rehabilitation to thereby reduce edema and increase blood flow.

It is another object of the invention to provide an ankle splint which can be molded to an ankle to stabilize the ankle against eversion and inversion while permitting dorsiflexion and planoflexion necessary for normal walking and therapeutic exercise.

It is another object of the invention to provide an ankle splint which can be custom-fitted to a particular patient.

It is another object of the invention to provide an ankle splint having a shape prior to forming which permits the splint to be formed onto either the left or the right ankle.

It is another object of the invention to provide an ankle splint which hardens in the presence of moisture to form a very rigid but very lightweight splint.

It is another object of the invention to provide an ankle splint which can be worn inside a shoe.

It is another object of the invention to provide a ankle splint which is stored in a moisture-proof pouch until ready for application to the ankle.

It is another object of the invention to provide an ankle splint which provides two splint segments which are releasably and adjustably attached together to form a splint.

It is another object of the invention to provide an ankle splint which is custom-molded to a patient's ankle in such a way that it can be initially held in place with an elastic bandage to reduce edema on the front of the foot, and thereafter held in place with straps during later stages of healing.

It is another object of the invention to provide an ankle splint which includes reinforced cushioning and protection for the ankle bones of the patient.

These and other objects of the present invention are achieved in the preferred embodiments disclosed below by providing an ankle splint product including an ankle splint for being custom-formed to the shape of an ankle while flexible and upon hardening providing a rigid, supporting custom fit an ankle splint product including an ankle splint for being custom-formed to the shape of an ankle while flexible and upon hardening providing a rigid, supporting custom fit. The ankle splint product comprises an outer container formed of moisture-impervious material and first and second flexible ankle splint segments positioned in the container in substantially moisture-free conditions and sealed therein against entry of moisture until use. Each of the first and second ankle splint segments comprises an elongate substrate, a reactive system impregnated into or coated onto the substrate, the system remaining stable when maintained in substantially moisture-free conditions and hardening upon exposure to moisture to form a rigid, self-supporting structure, an elongate, flexible protective pad positioned on one side of the substrate along its length to provide a cushioning barrier between the substrate and the skin of a patient when the ankle splint is in use; an elongate outer cover covering the substrate on a side opposite the protective pad. The substrate, protective pad, and outer cover are connected together into a unitary structure for being molded while flexible to an aspect of the lower leg. At least one elasticized strap is provided for being extended around the first and second splint segments and fastened to itself in tensioned condition for holding the first and second splint segments in conforming position on the lower leg and ankle and providing controlled compressive support to the lower leg and ankle.

According to one preferred embodiment of the invention, the strap comprises an elongate strap body having as least some longitudinally-extending elastic yarns for permitting compressive stretch along the length of the strap in conformance with the contour of the leg, and fastening means for securing the strap around the lower leg.

According to another preferred embodiment of the invention, the strap comprises an elongate strap member having as least some longitudinally-extending elastic yarns for permitting compressive stretch along the length of the strap in conformance with the contour of the leg, and fastening means for securing the strap member around the lower leg, wherein the fastening means comprises a buckle attached to one end of the strap member, and an end tab secured to an opposing end of the strap member for being received through the buckle and attached to the strap member.

According to yet another preferred embodiment of the invention, strap member includes one or the other of hook or loop material on a major surface thereof, and complementary hook or loop material carried by the end tab for being attached to the hook or loop material on the strap member.

According to yet another preferred embodiment of the invention, strap member includes a cushion insert having a first major surface overlying said protective pad and an opposing second major surface adapted for residing adjacent an ankle bone of the patient, the cushion insert cooperating with said protective pad to further protect and cushion the ankle of the patient when the ankle splint is in use.

According to yet another preferred embodiment of the invention, the splint product includes first and second like elasticized strap members for being extended around the first and second splint segments and fastened in tensioned condition at two vertically spaced-apart positions on the lower leg for holding the first and second splint segments in conforming position on the lower leg and ankle and providing controlled compressive support to the lower leg and ankle.

Preferably, the strap has a maximum elongation of approximately 25 percent.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
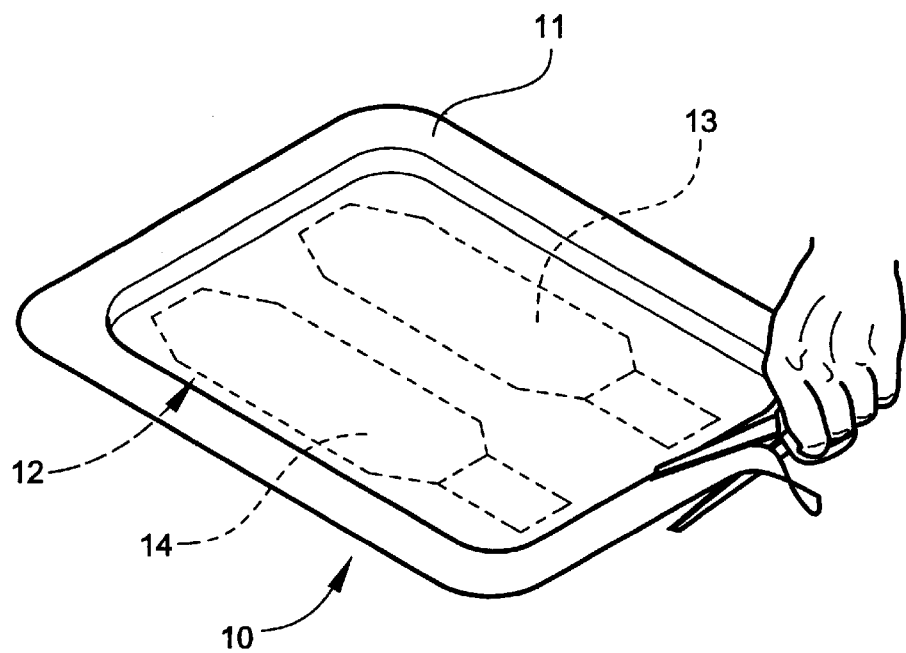
FIG. 1 illustrates the ankle splint product and removal of the ankle splint from the protective pouch.

Referring now specifically to the drawings, an ankle splint product according to a preferred embodiment of the invention is illustrated broadly at reference numeral 10. A sealed, moisture-impervious foil and plastic laminated pouch or container 11 is fabricated of a aluminum foil laminate having an outer tear resistant layer, a central aluminum foil layer and an inner heat sealable plastic layer. Container 11 is opened with scissors or a knife, and an ankle splint 12 according to an embodiment of the invention is removed.

Figure 2:
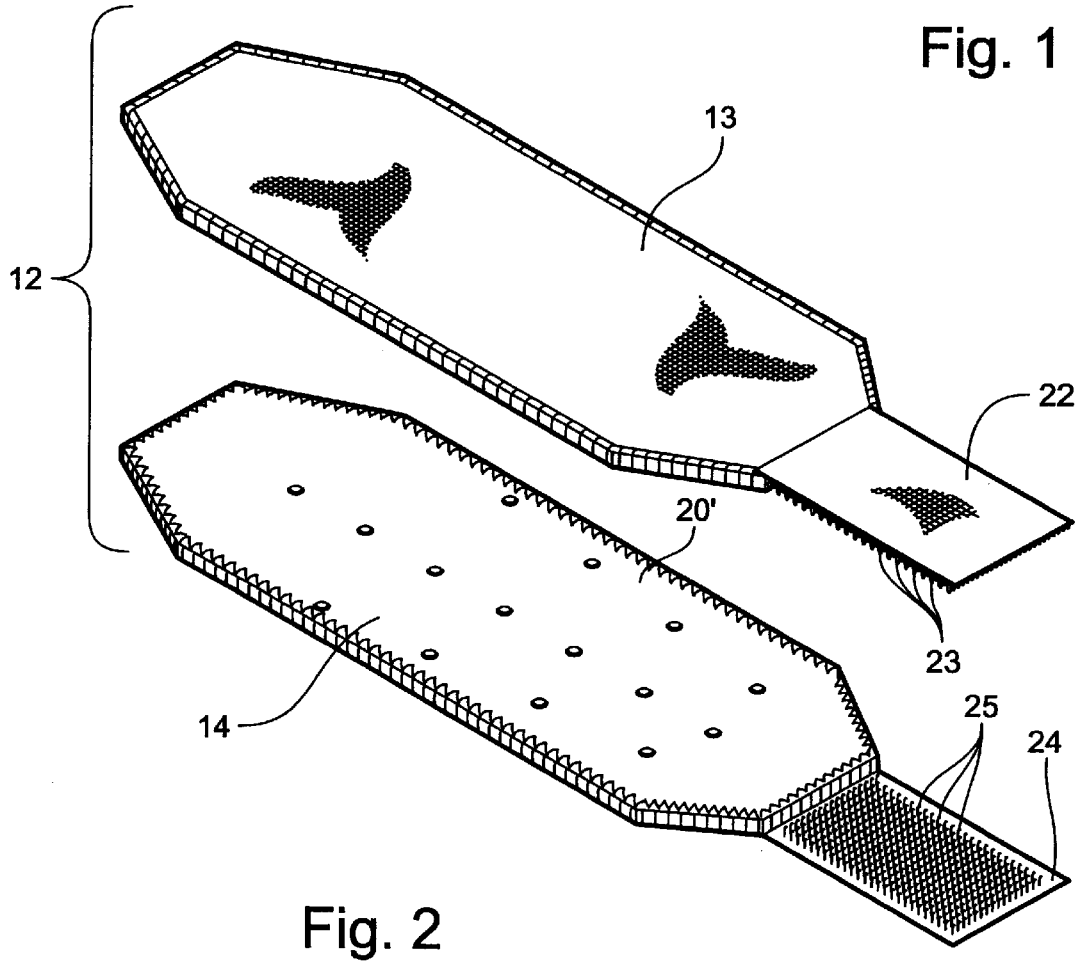
FIG. 2 is a perspective view showing an ankle splint segment of the ankle splint product according to an embodiment of the invention.

Ankle splint 12 is formed from first and second separate splint segments 13 and 14, as is shown in FIG. 2. Either of the splint segments 13 or 14 may be formed to the lateral or medial aspect of the ankle and lower leg. This interchangeability reduces manufacturing expense, inventory expense and simplifies application and replacement on the ankle after removal.

While it is preferable to place a splint segment 13 and 14 into a single container 11, each individual splint segment 13 and 14 may be placed in a separate container 11. This would allow, for example, replacement of one of the splint segments 13 or 14 while continuing to use the previously molded splint segment.

Figure 3:
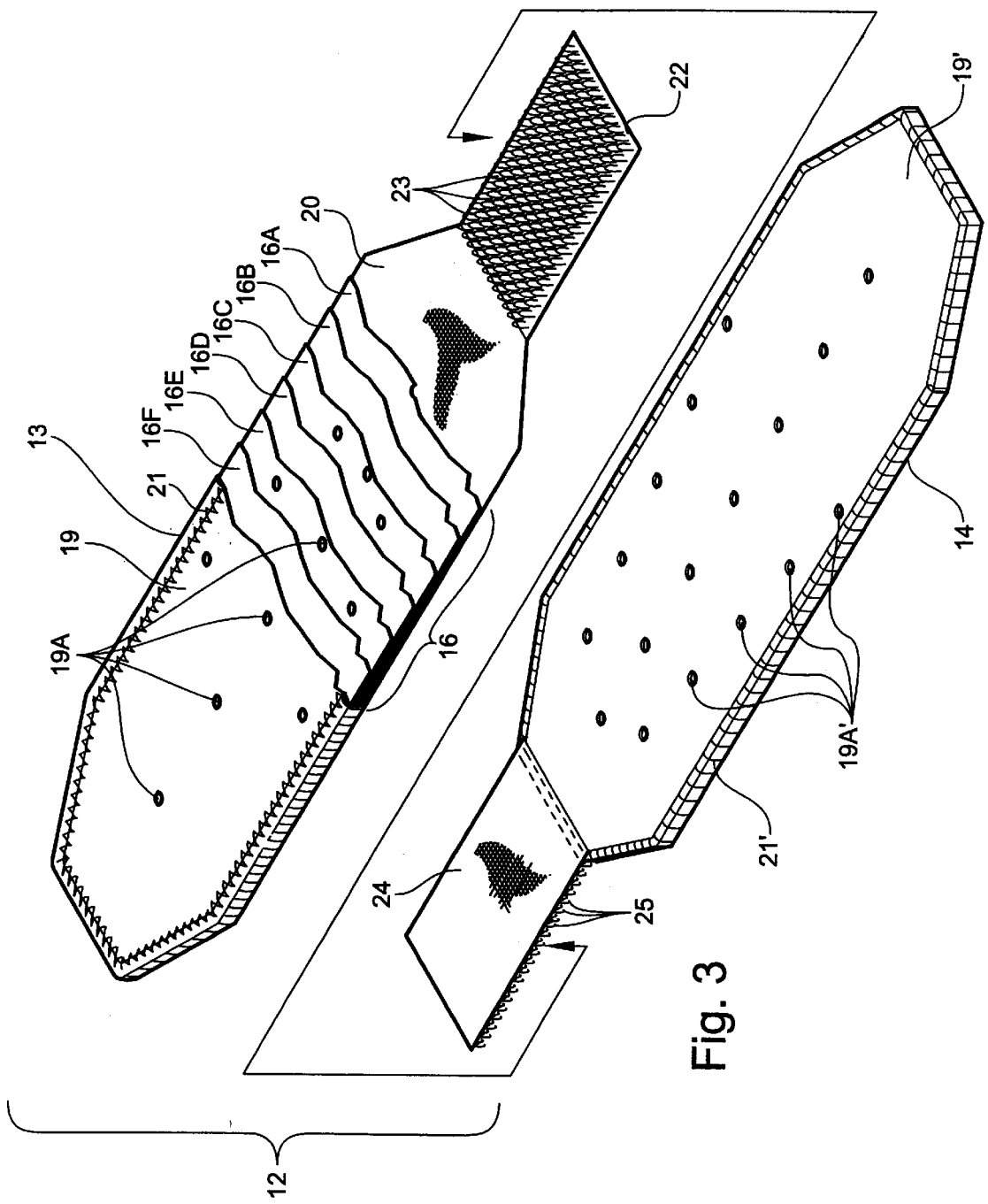
FIG. 3 is a perspective view of the ankle splint segment of FIG. 2, with parts broken away for clarity.

Referring now to FIG. 3, ankle splint segment 13 is illustrated and described more specifically. Ankle splint segment 13 includes a multilayer substrate 16 formed of, for example, six layers of woven fiberglass fabric 16A–F overlaid in registration with each other to form a laminated structure.

Other fabric material and constructions, such as knitted polypropylene, can also be used for the substrate fabric. The fiberglass fabric layers 16A–F of the substrate 16 are impregnated or coated with a moisture-curable resin such as polyisocyanate as described in full in the present applicant's U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. A typical formulation of the reactive system is set forth in the following table:

| Typical Formulation: | | | |
|---|---|---|---|
| Isonate ↓ 143L<br>Mondur ↓ CD<br>Rubinate ↓ XI168 | or<br>or | polyisocyanate | 50.0% |
| Pluracol ↓ P1010 | | polyol | 46.6% |
| DC-200 Silicone | | defoaming agent | 0.30% |
| Benzoyl Chloride | | stabilizer | 0.10% |
| Thancat ↓ DM-70 | | catalyst | 3.0% |
| | | | 100% |

A complete discussion of the parameters of the reactive system, the manner of production and the variables which apply are found in U.S. Pat. No. 4,411,262.

The polyisocyanate resin remains in a viscous, liquid unhardened state so long as the resin is not exposed to moisture. This permits the fiberglass layers 16A–F to remain flexible and moldable so long as the resin is not exposed to moisture, and for a relatively short period of time after exposure to moisture. The curing time can be controlled to some extent by the quantity and temperature of the water to which the resin is exposed. For example, exposure to water by dipping will result in quite rapid curing, while merely allowing the resin to be exposed to air will cause long curing times proportional to the amount of moisture in the air to which it is exposed.

Resin coated or impregnated fiberglass layers 16A–F are covered with a foam protective pad 19, which may be a single thickness or a laminated structure. One preferred embodiment is a 3/16 inch, six pound EVA (ethylene vinyl acetate) pad. Another embodiment may be a 3/8 inch laminated pad of a 1/8 inch outer EVA pad and a 1/4 inch outer polyethylene/polyurethane, combination open and closed cell foam. Spaced-apart ventilation holes 19A permit rapid penetration of water to the substrate 16 during wetting and curing, and permit improved air flow and cooling while being worn by the patient.

The pad 19 covers and provides cushioning between the skin and the rigid substrate 16. The pad 19 is flexible enough to bend easily with the other components of the ankle splint segment 13 during fitting and curing. The pad 19 extends the entire length of the ankle splint segment 13. The pad 19 and the substrate 16 are approximately the same thickness—on the order of about 4–6 mm.

A fabric outer cover 20, such as a woven polyester fabric, covers the side of the substrate 16 opposite the side covered by the foam pad 19. The fabric cover is sewn with, for example, an overedge or serging seam 21 directly to the edges of the foam pad 19 enclosing the substrate 16.

A patch 22 of male or female hook-and-loop material is sewn onto one end of the splint segment 13 defined as the bottom or heel end. As is shown in FIG. 3, loops 23 on one face of the patch 22 are positioned on the same side of the splint segment 13 as the pad 19.

As is shown in FIG. 2, the structure and shape of the splint segment 14 is essentially identical to that of the splint segment 13, this being noted throughout this application by reference numerals in prime notation. The only difference in splint segments 13 and 14 is a patch 24 of hook-and-loop material complementary to patch 22 is sewn onto one end of the splint segment 14. As is shown, the hooks 25 on one side of the patch 24 are positioned on the same side of the splint segment 14 as the fabric cover 20'. Because of this arrangement, when the side of the splint segments 13 and 14 having the pads 19 and 19', respectively, are placed against opposing medial and lateral aspects of the ankle, the loops 23 face upwardly and the hooks 25 face downwardly, thereby allowing attachment of the two splint segments 13 and 14 together to collectively form the splint 12. The patches 22 and 24 when attached form a heel stirrup 27 which provides some padding and protection to the heel while stabilizing the lower portion of the splint 12.

Figure 4:
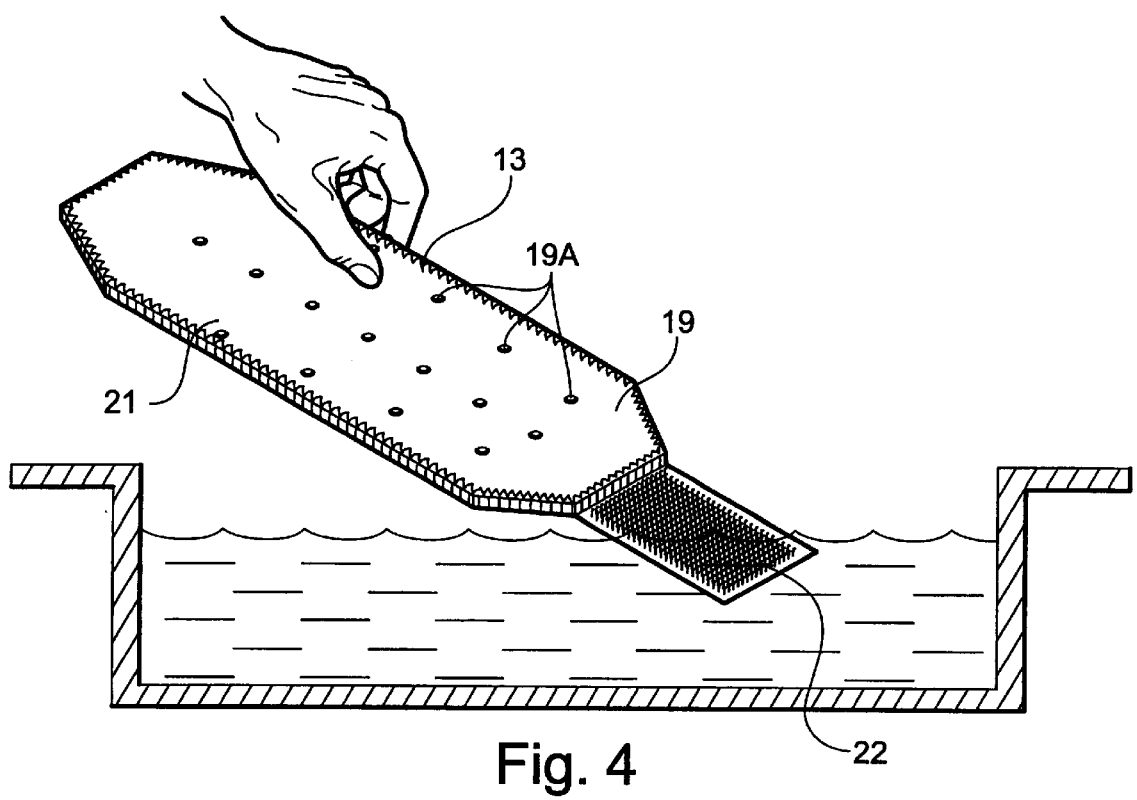
FIG. 4 illustrates that each ankle splint segment is wetted in water before application.

Referring now to FIGS. 4–11, preparation and application of the ankle splint 12 is illustrated. In FIG. 4, the ankle splint segments 13 and 14 have just been removed from the protective container 11 and the splint segment 13 is dipped in water to activate the moisture-curable resin described above. Immediately thereafter the splint segment 14 is likewise dipped in water.

Figure 5:
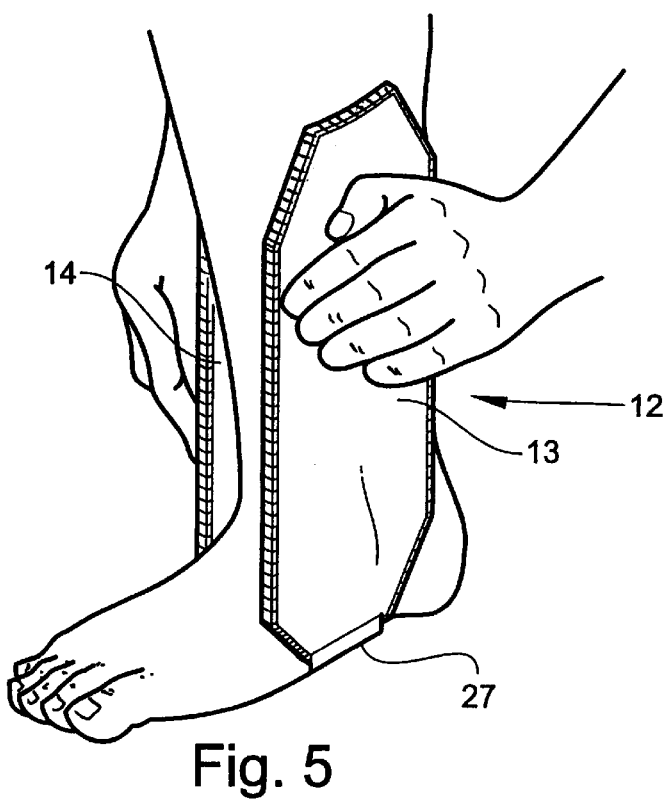
FIG. 5 is a perspective view illustrating application of two joined ankle splint segments to the ankle.

As shown in FIG. 5, the wetted and still flexible ankle splint segments 13 and 14 are attached together by marrying the hook-and-loop patches 22 and 24 to form the heel stirrup 27 and the splint 12. The splint 12 is immediately placed on the foot by positioning the heel of the patient directly onto the heel stirrup 27. Preferably, the splint segments 13 and 14 are each symmetrical along opposite sides of their longitudinal axis, so there is no defined forward or rearward side edge. The splint segments 13 and 14 of the splint 12 are then flexed upwardly along the lateral and medial aspects of the lower leg, as indicated by arrows 17 and 18 in FIG. 6, so that the splint segments 13 and 14 are positioned as shown. See also FIGS. 7 and 8. Note that ankle splint 12 is usable on either the right or left foot.

The ankle splint 12 is held in place so that as the curing takes place the exact conformation of the ankle and leg is transferred to the ankle splint 12. The ankle splint 12 will harden within a matter of minutes, and will permanently retain the conformation in which it was held during curing. The fit is close and exact. With no voids to fill or accommodate as the patient moves about, complete and even protection to the body is provided. The pressure exerted by the splint 12 is very evenly spread over the maximum practical surface area, thereby reducing the possibility of chafing, rubbing or blistering at points of uneven pressure.

Note, also, that the heel stirrup 27 remains flexible after the splint segments 13 and 14 cure and harden. Removal and replacement of the splint 12 is facilitated since the custom-formed splint segments 13 and 14 easily fold away from the ankle, using the heel stirrup 27 as a hinge.

Figure 6:
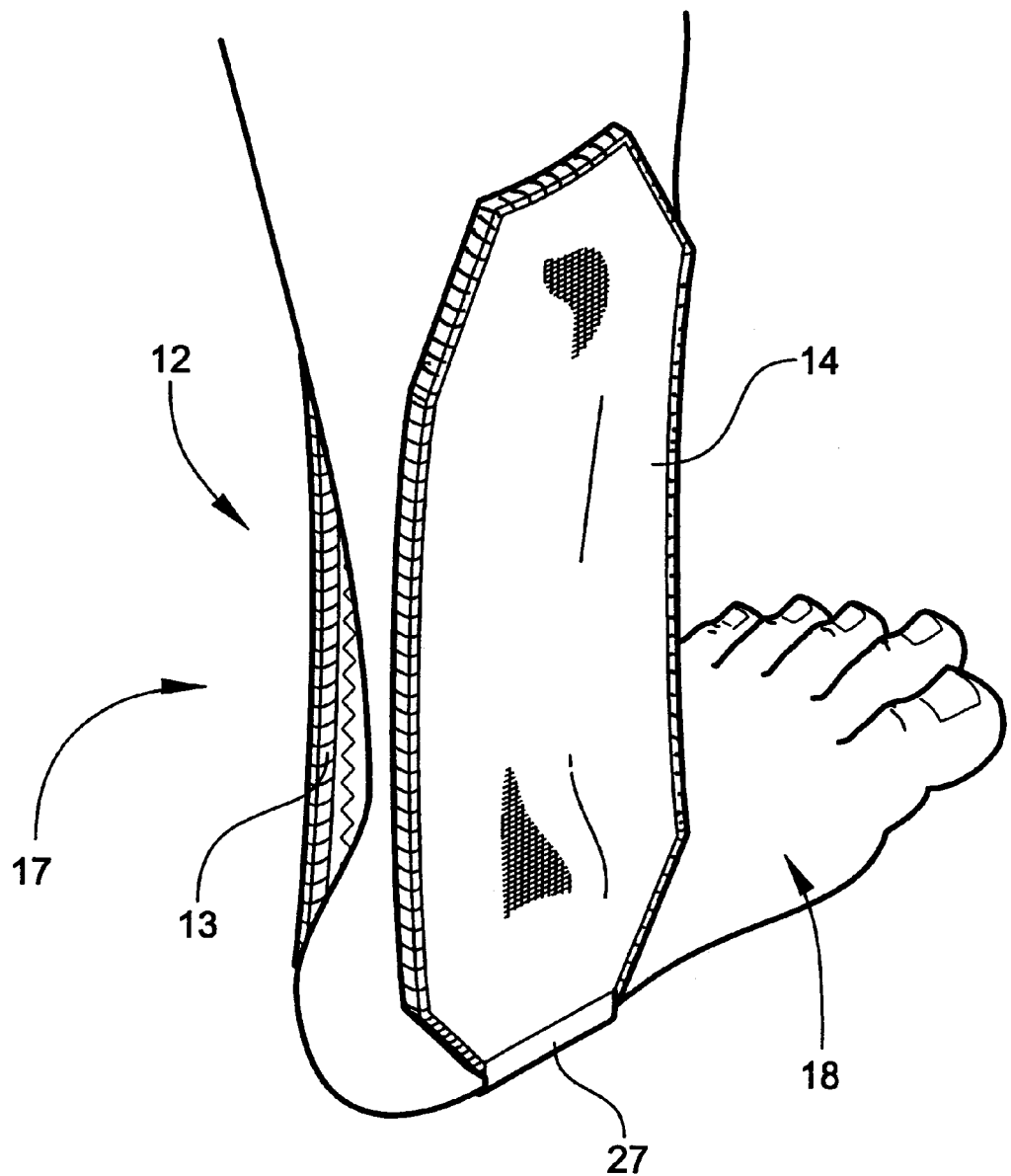
FIG. 6 is a perspective view illustrating from the rear the ankle splint in place on the ankle.
Figure 7:
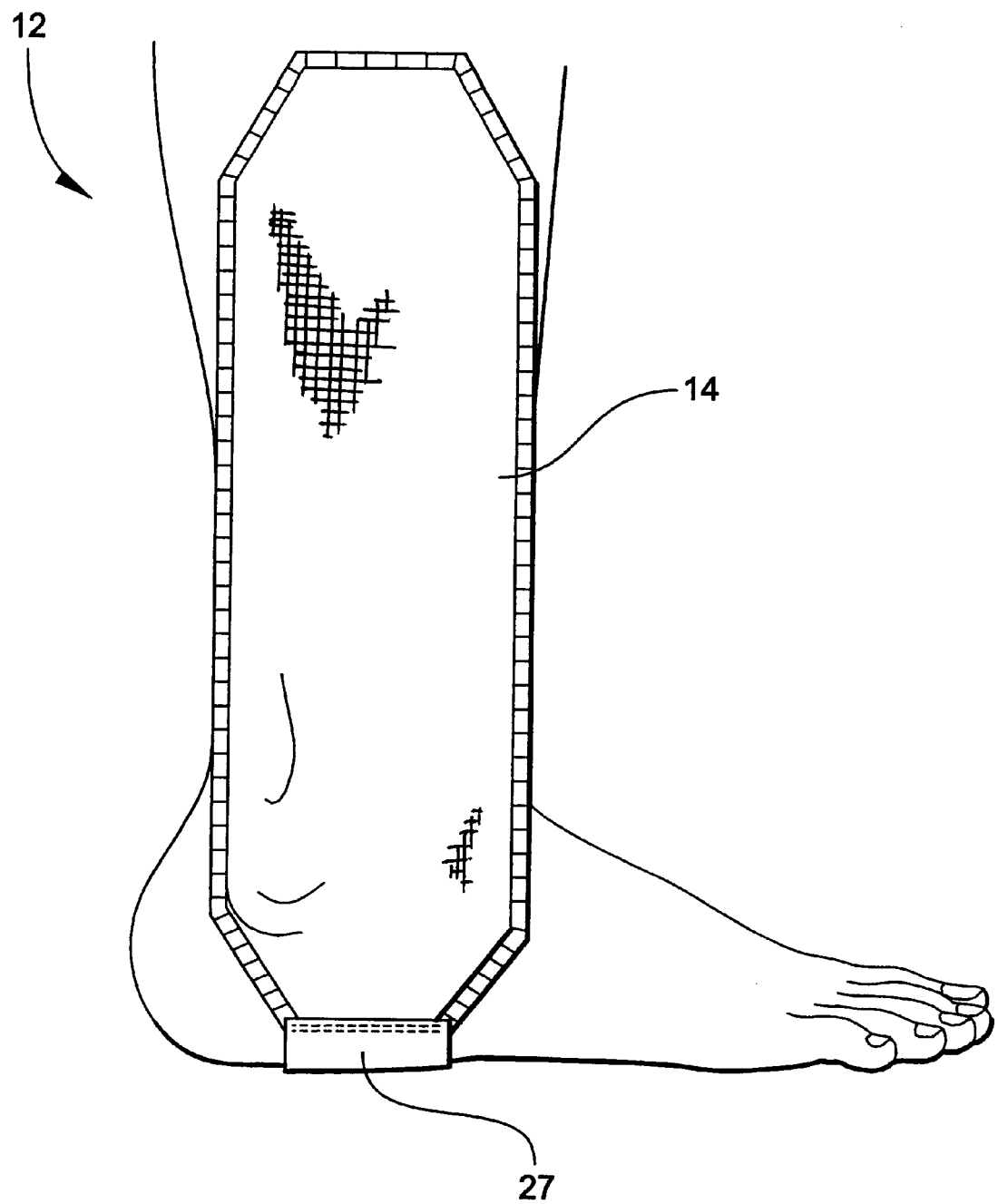
FIG. 7 is a side elevation of the ankle splint in place on the ankle.
Figure 8:
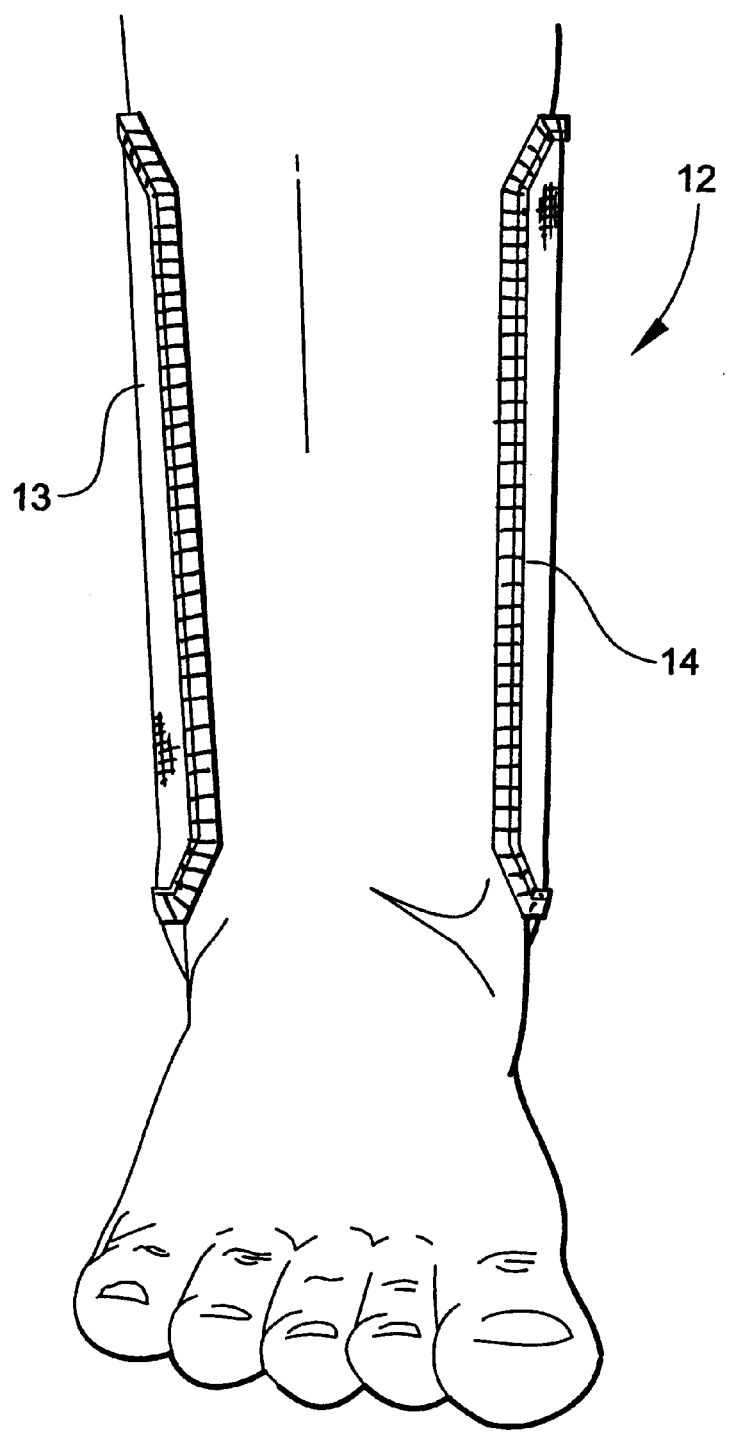
FIG. 8 is a front elevation of the ankle splint in correct position on the ankle.

As is shown in FIGS. 6 and 8, a properly applied ankle splint 12 splints the medial and lateral aspects of the ankle and foot with minimal coverage of the front or rear of the foot or leg. Thus, eversion and inversion of the foot is prevented while permitting substantially unrestricted dorsiflexion and planoflexion necessary for normal walking and therapeutic exercise, and an enhanced ability to place the foot into a normal shoe. Typically, a relatively soft shoe, such as an athletic shoe will accommodate the ankle splint 12 easily, it being necessary only to loosen the laces to permit added width to the shoe.

Figure 9:
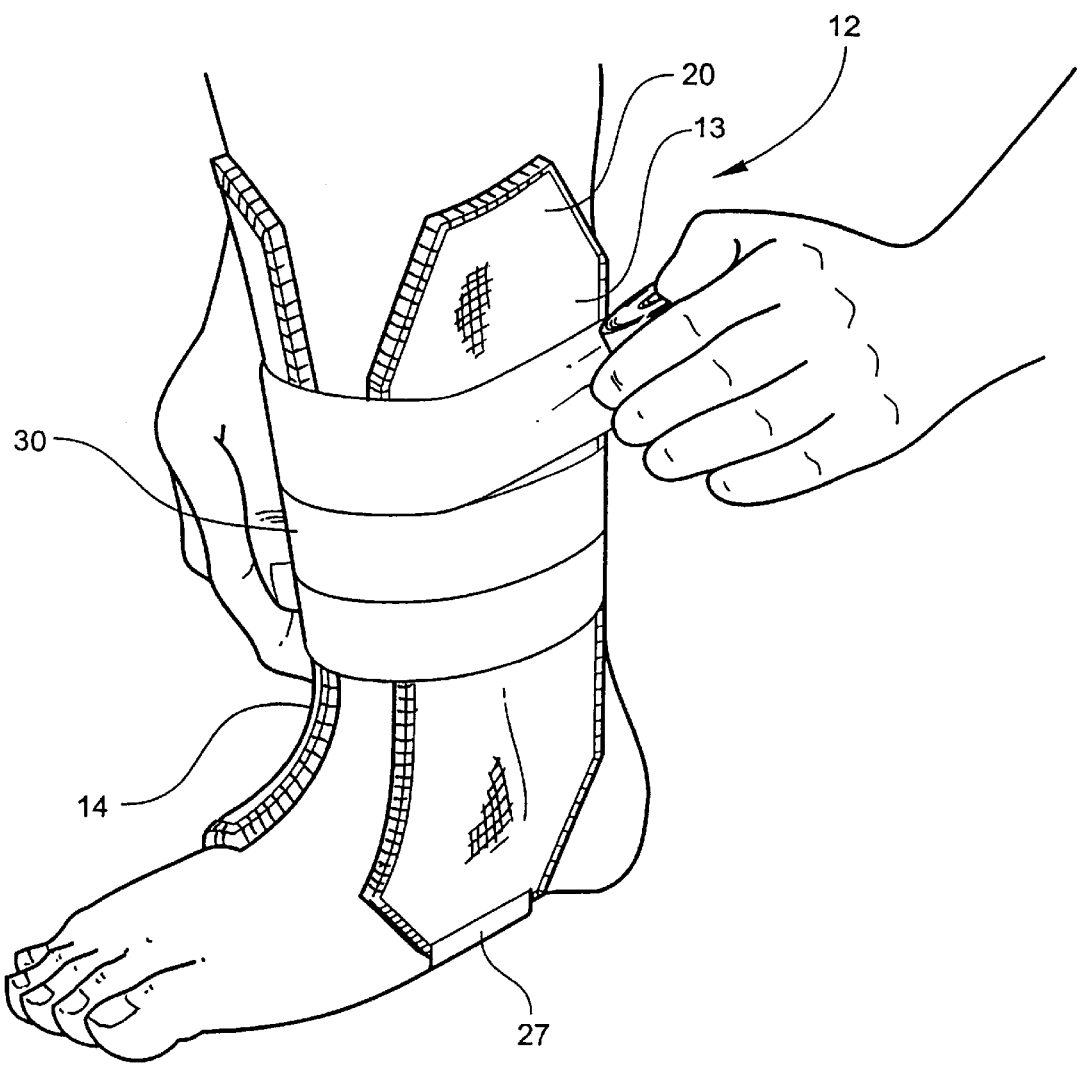
FIG. 9 is a perspective view showing that the ankle splint is preferably wrapped to hold it in place during curing and during wear.
Figure 10:
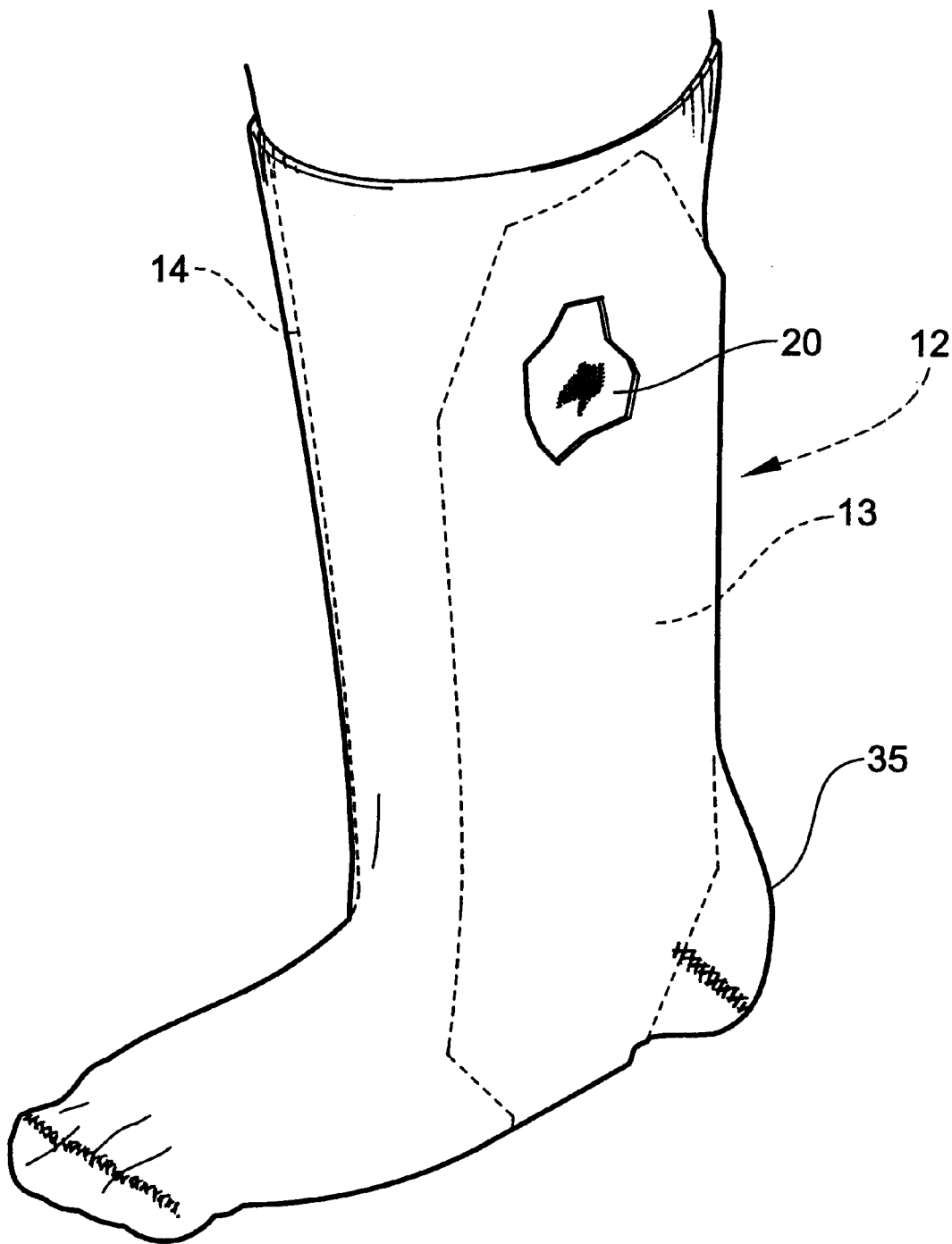
FIG. 10 is a perspective view, with parts broken away for clarity, of the ankle splint being worn under a sock.

As is shown in FIG. 9, the ankle splint 12 may be held in place during curing by a wrapping, such as a conventional elastic medical bandage 30. Such a bandage may also be worn during treatment as a way of maintaining a close fit of the ankle splint 12 against the foot and leg. This has been found to reduce edema in the front of the foot during the early stages of recovery, when pressure applied by the splint 12 to the sides of the ankle might otherwise force fluid to the front of the foot. A sock 35 may also be used to hold the ankle splint 12 in place during hardening, as is shown in FIG. 10.

Figure 11:
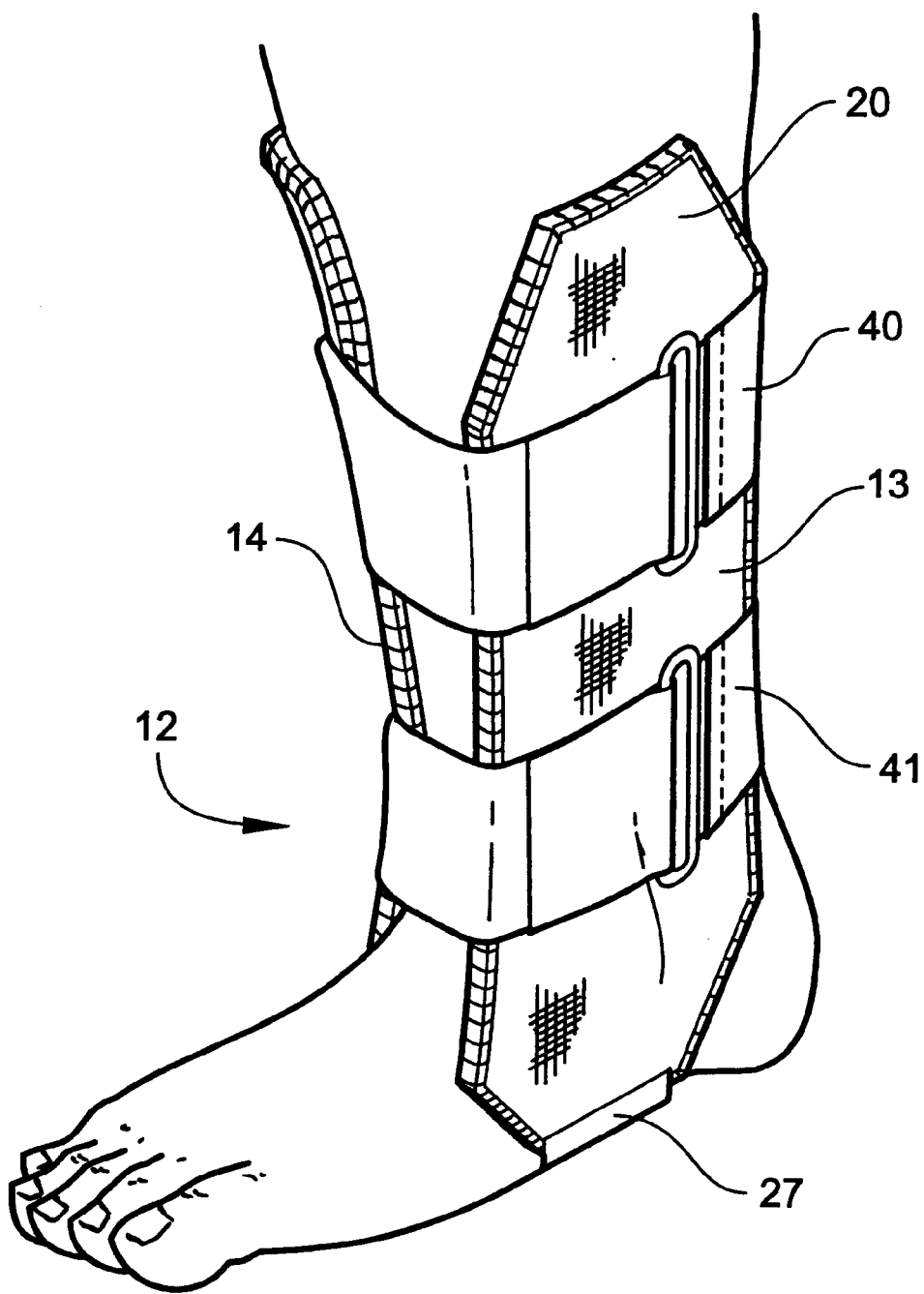
FIG. 11 is a perspective view showing that the ankle splint may be held in place with straps during curing and during wear.

Straps such as elastic straps or straps with hook and loop fasteners such as straps 40 and 41 may be used to hold the ankle splint 12 in place during treatment, as is shown in FIG. 11. These straps preferably may be separate elements, like straps 40 and 41, or may be sewn onto the ankle splint 12 during manufacture.

As noted above, the heel stirrup 27 remains flexible, so some form of support is required to hold the splint 12 in supporting position against the ankle. The relative thinness and compactness of the splint 12 permits a wide variety of supports, including even a high-topped shoe or boot.

In one preferred embodiment suitable for children and adults of small stature, each ankle splint segment 13 or 14 has an overall length of 30 cm, an overall width of 9 cm at a point one-half of the distance between the upper and lower ends and taper to a width of 5 cm at each end. The heel stirrup is preferably 5 cm wide and each of the hook-and-loop patches 22 and 24 are 7 cm long.

In another preferred embodiment suitable for adults of medium and large stature, each ankle splint segment 13 or 14 has an overall length of 35 cm, an overall width of 10 cm at a point one-half of the distance between the upper and lower ends and taper to a width of 5 cm at each end. The heel stirrup is preferably 5 cm wide and each of the hook-and-loop patches 22 and 24 are 7 cm long. The ends of the splint segments 13 and 14 may be rounded rather than tapered as shown in the drawings and described herein. In addition, other forms of cushion padding, such as air bladders, gel-filled bladders or other types of foam or matrix products may be used. The approximate thickness of the body of the ankle splint 12 in both sizes is 8 mm, and of the hook-and-loop patches 22 and 24—2 mm.

Figure 12:
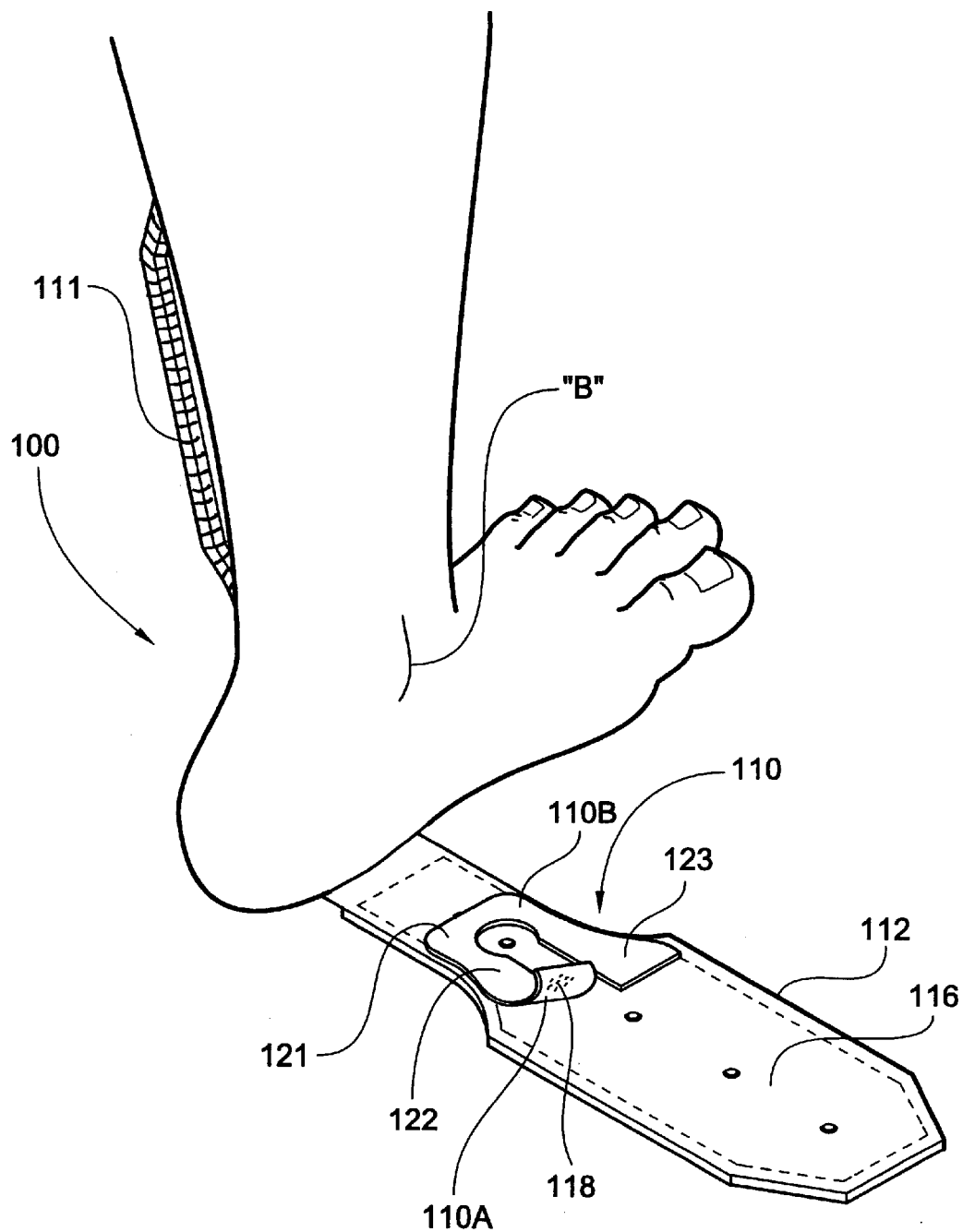
FIG. 12 is a perspective view of an ankle splint according to a modified embodiment of the invention with one of the splint segments folded down to show the attachment of the cushion insert to the protective pad.
Figure 13:
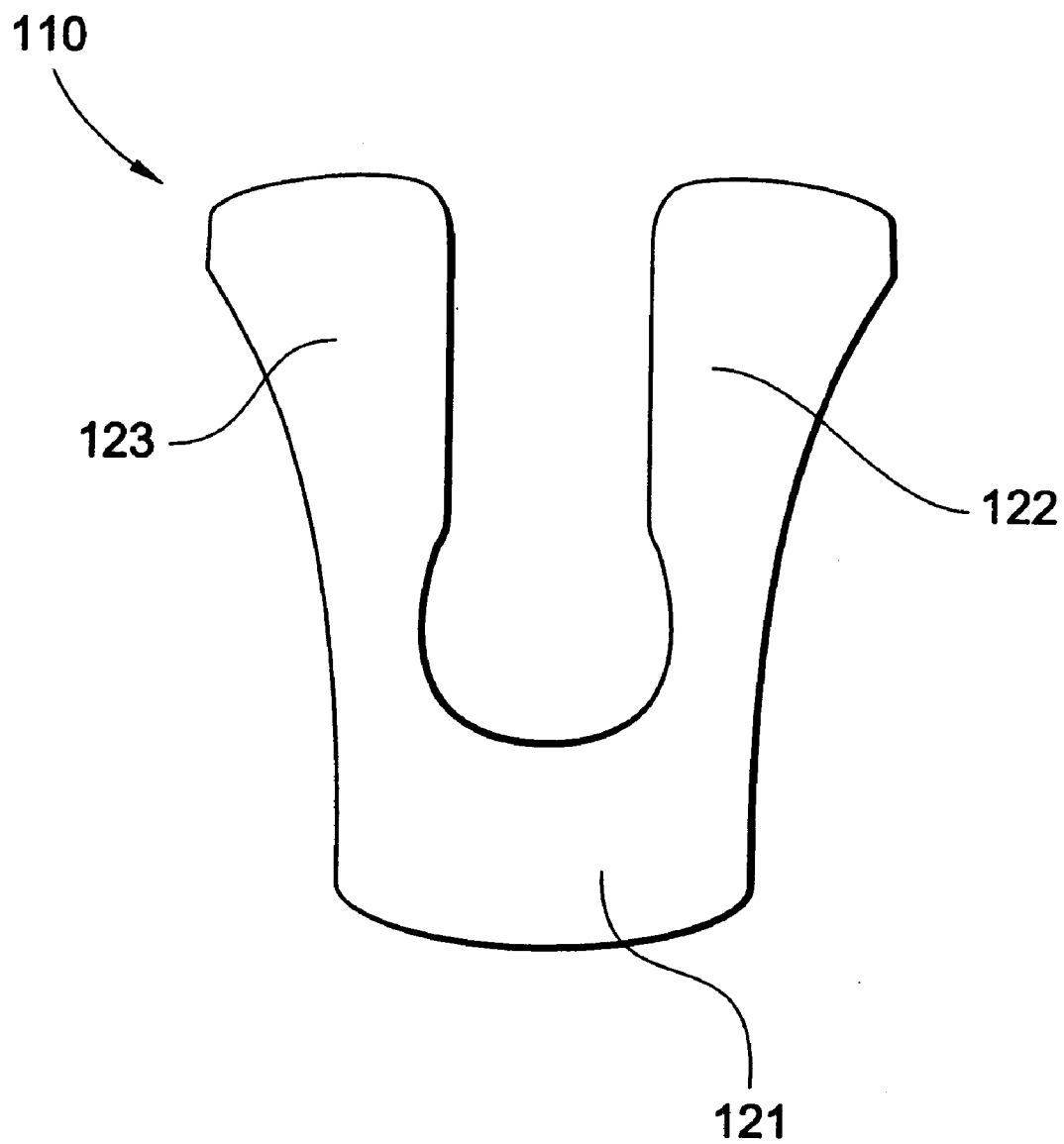
FIG. 13 is an elevational view of the cushion insert.
Figure 14:
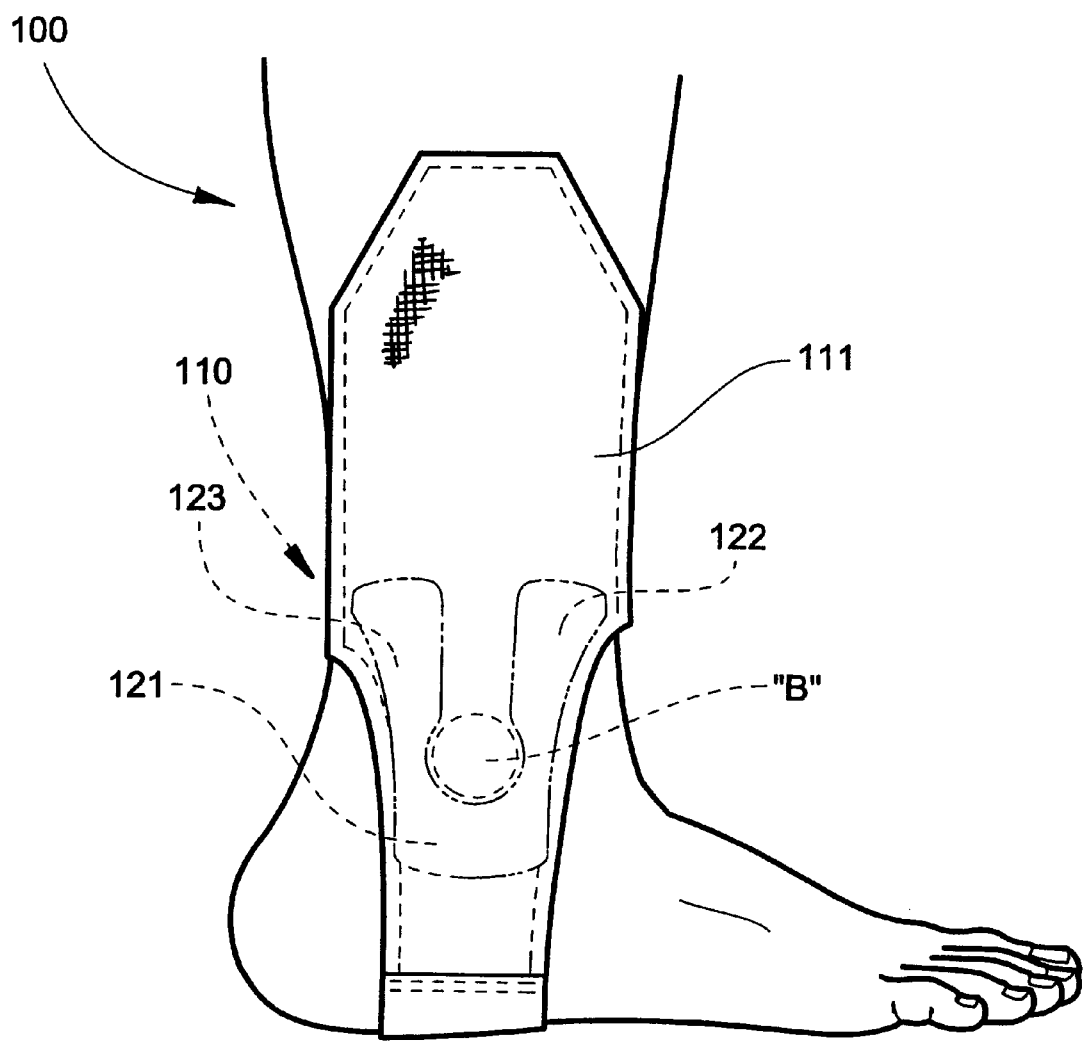
FIG. 14 is an elevational view of the ankle splint, in use, and showing the cushion insert and ankle bone of the patient in phantom.

Referring now to FIGS. 12–14, an ankle splint 100 according to the invention further includes one or two separately attached foam cushion inserts 110 positioned, respectively, to reside adjacent one or both of the medial and lateral ankle bones "B" of the patient to further protect and cushion the ankle when the splint 100 is being used. The medial ankle bone "B" is shown in FIG. 12. The ankle splint 100 is formed of splint segments 111 and 112 constructed as described above with reference to splint segments 13 and 14. The reference herein to medial and lateral "ankle bones" means the lower prominences of the tibia and fibula, respectively, also known as the "malleoluses."

As shown in FIG. 12, the cushion insert 110 has an inside major surface 100A which overlies the protective pad 116 of the splint segment 112 and includes a pressure-sensitive adhesive coating 118. After molding the splint segment 112 to the ankle, as previously described, the molded segment 112 is folded away from the ankle and the insert 110 placed in an area of the pad 116 residing adjacent the ankle bone "B" of the patient when the splint 100 is being used. Light application of pressure to an outside major surface 110B of the insert 110 activates the pressure-sensitive adhesive coating 118 which holds the insert 110 in place as the splint segment 112 is returned to its in-use position against the ankle. The adhesive coating 118 allows convenient removal and repositioning of the insert 110 for custom placement to suit the individual patient, and replacement of the insert 110 when worn. The outside major surface 110B of the insert 110 is adapted to reside against the skin of the patient.

As best shown in FIGS. 13 and 14, the cushion insert 110 is generally U-shaped with an open central area defined by a base 121 and opposing integrally-formed extensions 122 and 123. The term "U-shaped" is defined broadly herein to include, for example, structure which is generally V-shaped or horseshoe-shaped. When the splint 100 is in use, the base 121 of the insert 110 resides directly adjacent a lower portion of the ankle bone "B" with the extensions positioned on opposite sides of the ankle bone "B". The open central area provides space for accommodating the ankle bone "B" and for reducing pressure applied by the splint segments 111 and 112. According to one embodiment, the cushion insert 110 is formed of flexible, ¼-inch thick polycushion foam with an overall height of 3.28 inches and an overall width of 2.54 inches. One cushion insert 110 is preferably used per splint segment 111 and 112 for each of the medial and lateral ankle bones of the patient.

Figure 15:
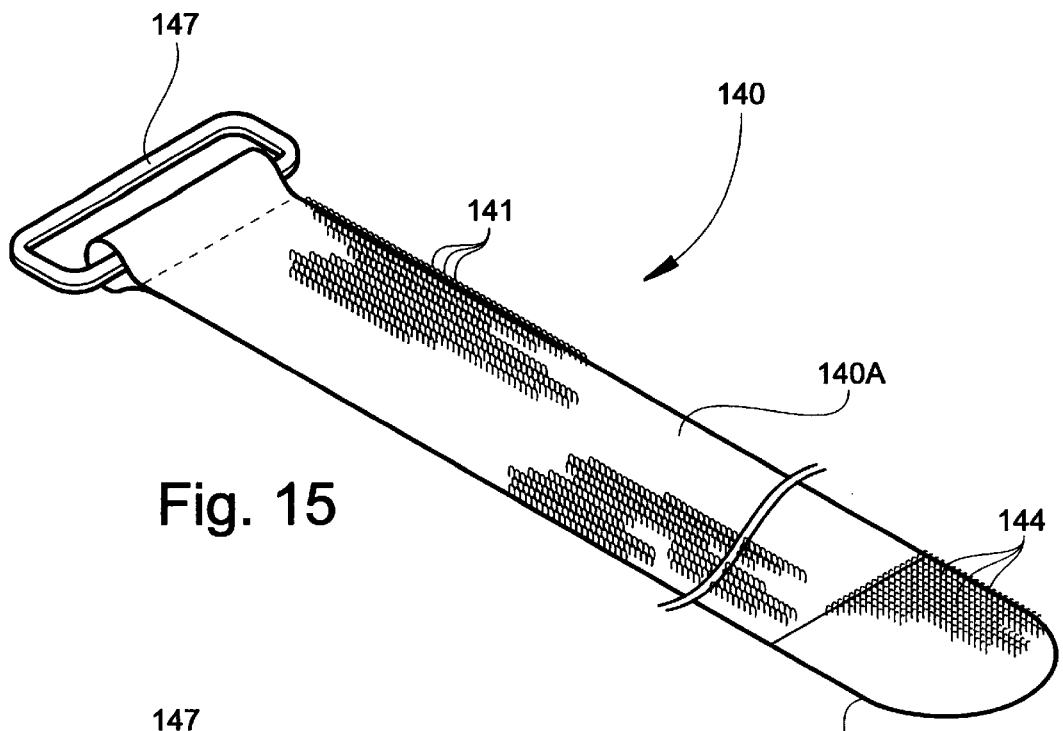
FIG. 15 is a perspective view of a elasticized strap used with the splint product according to an embodiment of the invention.
Figure 16:
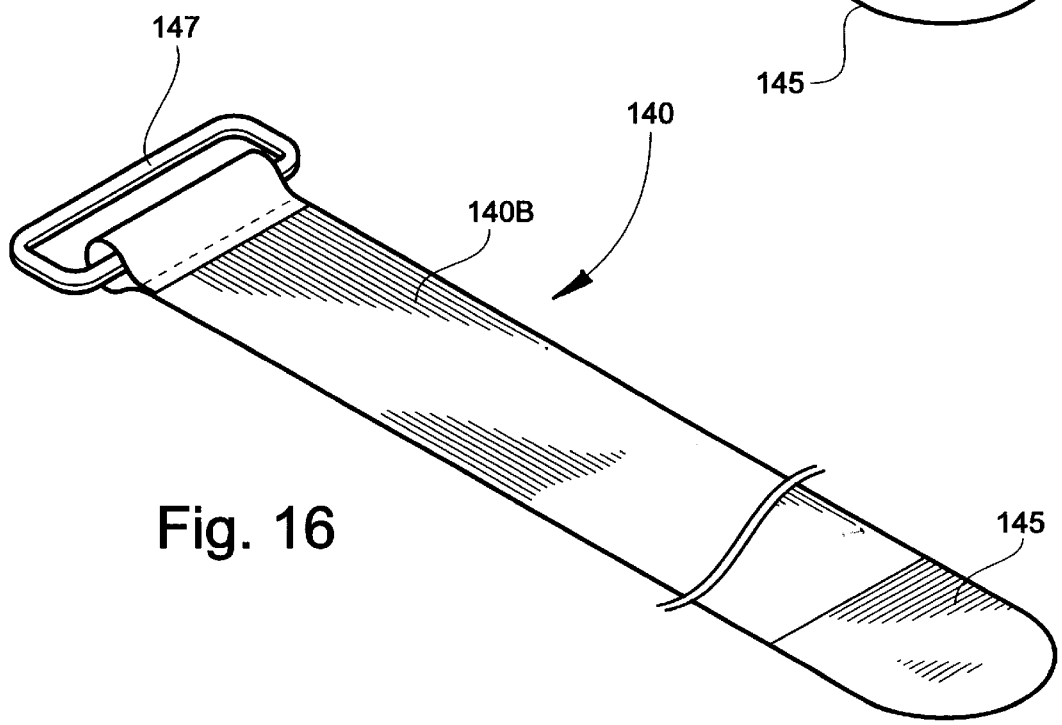
FIG. 16 is a perspective view of the reverse side of the elasticized strap shown in FIG. 15.

Referring now to FIGS. 15 and 16, an elasticized strap 140 is shown. Strap 140 has opposing major sides 140A and 140B. Side 140B is covered with loops 141 which cooperate with hooks 144 which cover one side of an end tab 145. A buckle 147 is secured to the end of the strap 140 opposite the end tab 145 and permits the strap 140 to be formed into a closed loop by passing the end tab 145 through the buckle 147, folding the strap 140 onto itself and engaging the hooks 144 with the loops 141 at the desired position.

Figure 17:
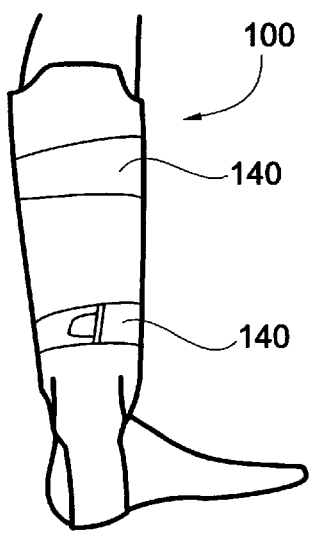
FIGS. 17, 18 and 19 are sequential views showing flexing and relaxing of the lower leg muscles during walking and the conformability of the splint product to the lower leg.
Figure 18:
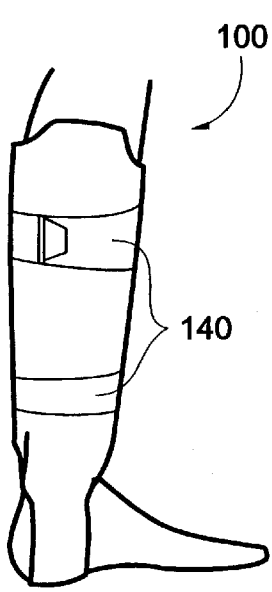
Figure 19:
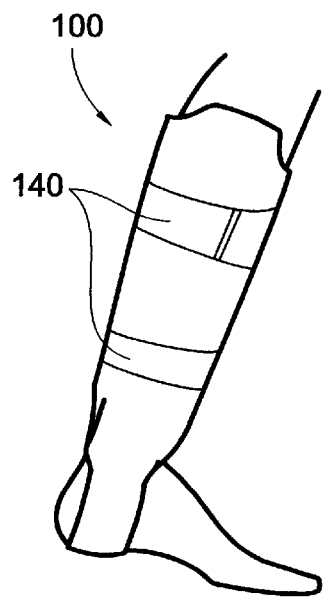

As is shown in FIGS. 17, 18 and 19, two straps 140 are preferably used to hold the splint segments 13, 14 (FIGS. 1–11) and the splint segments 111 and 112 (FIGS. 12–14) against the lateral and medial aspects of the lower leg. Straps 140 provide significant advantages over the use of long elastic bandages. Such elastic bandages are sometimes more suitable for severe injuries and during the initial phases of healing when complete or almost complete immobilization of the injured limb is required. The elastic bandages such as the elastic bandage shown 30 shown in 9 cover substantially the entire length of the splint segments 13, 14 or 111, 112 and therefore significantly restricts movement of the foot and leg. The bandage 30 also require some time and practice to apply properly. There is a danger of overtightening, since such products have elongations of 100 percent or more.

However, once the patient begins rehabilitation, increased movement of the limb is essential. Non-elastic straps of the type furnished with prior art devices do not conform to the generally conical shape of the lower leg. Thus, either the top or the bottom of the strap is too loose or too tight. Non-elastic straps merely hold the splint in place, but provide no additional benefits to the patient. As the patient walks and the leg changes size and shape, the strap is not permitted to also change to accommodate these changes.

In contrast, strap 140 includes up to about 25 percent longitudinal elasticity, although the strap 140 will ordinarily be placed on the leg with no more than about 5–10 percent elongation. Thus, the top and bottom edges of the strap 140 may elongate independently of each other to precisely conform to the shape and circumference of the leg at the point of contact. This elasticity permits increased movement by the patient. As the patient walks, the calf and other muscles of the lower leg and foot contract and relax, varying somewhat the circumference and shape of the lower leg. For example, as shown in FIGS. 17, 18 and 19, the usual three-position step causes the calf muscle to alternately relax (FIG. 17) and flex (FIG. 19) as the foot and leg move through its range of motion. The elasticity of the strap 140 permits the calf muscle to stretch the strap 140 slightly and progressively (FIGS. 18 and 19) during each step. When the muscle is relaxed, the strap 140 contracts against the muscle. This repetitive pumping action helps milk out edema and increase blood flow. This not only speeds healing, but may reduce the possibility of phlebitis which can sometimes result from prolonged immobilization of or unyielding pressure on the limb.

The use of two straps 140 in vertically spaced-apart position on the leg, as shown in FIGS. 11, and 17–19 permits the straps 140 to be adjusted individually to vary the desired pressure and enhance comfort, since most of the dorsal and ventral aspects of the leg are open to air circulation.

As is apparent from the foregoing, the straps 140 may be very quickly secured around the leg, removed and adjusted as needed.

An ankle splint product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. An ankle splint product including an ankle splint for being custom-formed to the shape of an ankle while flexible and upon hardening providing a rigid, supporting custom fit, said ankle splint product comprising:
   (a) an outer container formed of moisture-impervious material;
   (b) first and second flexible ankle splint segments positioned in the container in substantially moisture-free conditions and sealed therein against entry of moisture until use, each of the first and second ankle splint segments comprising:
      (i) an elongate substrate;
      (ii) a reactive system impregnated into or coated onto the substrate, the system remaining stable when maintained in substantially moisture-free conditions and hardening upon exposure to moisture to form a rigid, self-supporting structure;
      (iii) an elongate, flexible protective pad positioned on one side of the substrate along its length to provide a cushioning barrier between the substrate and the skin of a patient when the ankle splint is in use;
      (iv) an elongate outer cover covering the substrate on a side opposite the protective pad; and
      (v) said substrate, protective pad, and outer cover being connected together into a unitary structure for being molded while flexible to an aspect of the lower leg; and
   (d) at least one elasticized strap for being extended around the first and second splint segments and fastened to itself in tensioned condition for holding the first and second splint segments in conforming position on the lower leg and ankle and providing controlled compressive support to the lower leg and ankle.

2. An ankle splint product according to claim 1, wherein said strap comprises:
   (a) an elongate strap body having as least some longitudinally-extending elastic yarns for permitting compressive stretch along the length of the strap in conformance with the contour of the leg; and
   (b) fastening means for securing the strap around the lower leg.

3. An ankle splint product according to claim 1, wherein said strap comprises:
   (a) an elongate strap member having as least some longitudinally-extending elastic yarns for permitting compressive stretch along the length of the strap in conformance with the contour of the leg; and
   (b) fastening means for securing the strap member around the lower leg, said fastening means comprising:
      (i) a buckle attached to one end of the strap member; and
      (ii) an end tab secured to an opposing end of the strap member for being received through the buckle and attached to the strap member.

4. An ankle splint product according to claim 3, wherein said strap member includes:
   (a) one or the other of hook or loop material on a major surface thereof; and
   (b) complementary hook or loop material carried by the end tab for being attached to the hook or loop material on the strap member.

5. An ankle splint product according to claim 4, wherein said strap member includes a cushion insert having a first major surface overlying said protective pad and an opposing second major surface adapted for residing adjacent an ankle-bone of the patient, said cushion insert cooperating with said protective pad to further protect and cushion the ankle of the patient when the ankle splint is in use.

6. An ankle splint product according to claim 1, 2, 3, 4 or 5, wherein said splint product includes first and second like elasticized strap members for being extended around the first and second splint segments and fastened in tensioned condition at two vertically spaced-apart positions on the lower leg for holding the first and second splint segments in conforming position on the lower leg and ankle and providing controlled compressive support to the lower leg and ankle.

7. An ankle splint product according to claim 1, 2, 3, 4 or 5, wherein said strap has a maximum elongation of approximately 25 percent.

* * * * *